United States Patent
Kumar et al.

(10) Patent No.: US 10,607,719 B2
(45) Date of Patent: Mar. 31, 2020

(54) ROBUST VARIANT IDENTIFICATION AND VALIDATION

(71) Applicant: KONINKLIJKE PHILIPS N.V., Eindhoven (NL)

(72) Inventors: Sunil Kumar, Bangalore (IN); Randeep Singh, Bangalore (IN); Biswaroop Chakrabarti, Kolkata (IN); Subodh Kumar, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 1485 days.

(21) Appl. No.: 14/363,436

(22) PCT Filed: Dec. 3, 2012

(86) PCT No.: PCT/IB2012/056911
§ 371 (c)(1),
(2) Date: Jun. 6, 2014

(87) PCT Pub. No.: WO2013/084133
PCT Pub. Date: Jun. 13, 2013

(65) Prior Publication Data
US 2014/0336999 A1     Nov. 13, 2014

Related U.S. Application Data

(60) Provisional application No. 61/568,336, filed on Dec. 8, 2011.

(30) Foreign Application Priority Data

Dec. 14, 2011 (EP) ...................... 11193585

(51) Int. Cl.
*G16B 40/00* (2019.01)
*G16B 20/00* (2019.01)
*G16B 30/00* (2019.01)

(52) U.S. Cl.
CPC ............. *G16B 40/00* (2019.02); *G16B 20/00* (2019.02); *G16B 30/00* (2019.02)

(58) Field of Classification Search
None
See application file for complete search history.

(56) References Cited

U.S. PATENT DOCUMENTS

2013/0338934 A1* 12/2013 Asadi ...................... G06F 19/22
702/20

FOREIGN PATENT DOCUMENTS

CN    101131391 A    2/2008
EP    2101275 A1    10/2008

OTHER PUBLICATIONS

Prachi Kothiyal (Detection and Classification of Sequence Variants for Diagnostic Evaluation of Genetic Disorders, Dissertation at University of Cincinnati, Biomedical Engineering, Proquest, 2010, pp. 1-93).*
Harismendy, O. "Evaluation of next generation sequencing platforms for population targeted sequencing studies." Genome Biology ,vol. 10:R32 (2009).
Wang, J. et al. "The diploid genome sequence of an Asian individual", Nature. vol. 456, pp. 60-65 (2008).
Breslauer, K.J.. "Predicting DNA duplex stability from the base sequence", Proc Natl Acad Sci USA. Jun. 1986; 83 (11:3746-50.
Sivolob, A.V. Translational positioning of nucleosomes on DNA: the role of sequence-dependent isotropic DNA bending stiffness, J. Mol Biol. Apr. 14, 1995;247(5):918-31.
Li, H. et al. "Fast and accurate short read alignment with Burrow-Wheelers transform". Bioinformatics, 25, 1754-1760 (2009).
Li, H. et al. The Sequence Alignment/Map (SAM) Format and SAMtools. Bioinformatics, (2009).
Matukumalli, L.K. et al. "Application of machine learning in SNP discovery", BMC Bioinformatics, Biomed Central, London, GB. vol. 7, No. 1, Jan. 6, 2006, p. 4.
Kong, E. et al. "Predicting single nucleotide polymorphisms (SNP) from DNA sequence by support vector machine", Frontiers in Bioscience, vol. 12, No. 1, Jan. 1, 2007, p. 1610.
Hu, X. et al. "Evaluation of the occurrence possibility of SNP in *Brassica napus* with sliding window features by using RBF networks". WUHAN University Journal of Natural Sciences, vol. 16, No. 1, Feb. 1, 2011, pp. 73-78.
Chen, et al., "Combining SVMs with Various Feature Selection Strategies", Internet Citation, Jul. 11, 2005, pp. 1-10, Department of Computer Science, National Taiwan University; retrieved from URL;http://www.csie.ntu.edu.tw/~cjlin/papers/features.pdf.

* cited by examiner

*Primary Examiner* — John S Brusca

(57) ABSTRACT

A non-transitory storage medium stores an assembled genetic sequence comprising aligned sequencing reads. An electronic processing device is configured to perform operations including: identifying a possible variant in the assembled genetic sequence; computing value of at least one read property for reads of the assembled genetic sequence; and calling the possible variant conditional upon the computed values of the at least one read property for sequencing reads of the assembled genetic sequence that include the possible variant satisfying an acceptance criterion. The electronic processing device may be further configured to select at least one region of the assembled genetic sequence for validation based on a non random selection criterion.

16 Claims, 5 Drawing Sheets

ROBUST VARIANT IDENTIFICATION AND VALIDATION

Figure 1:
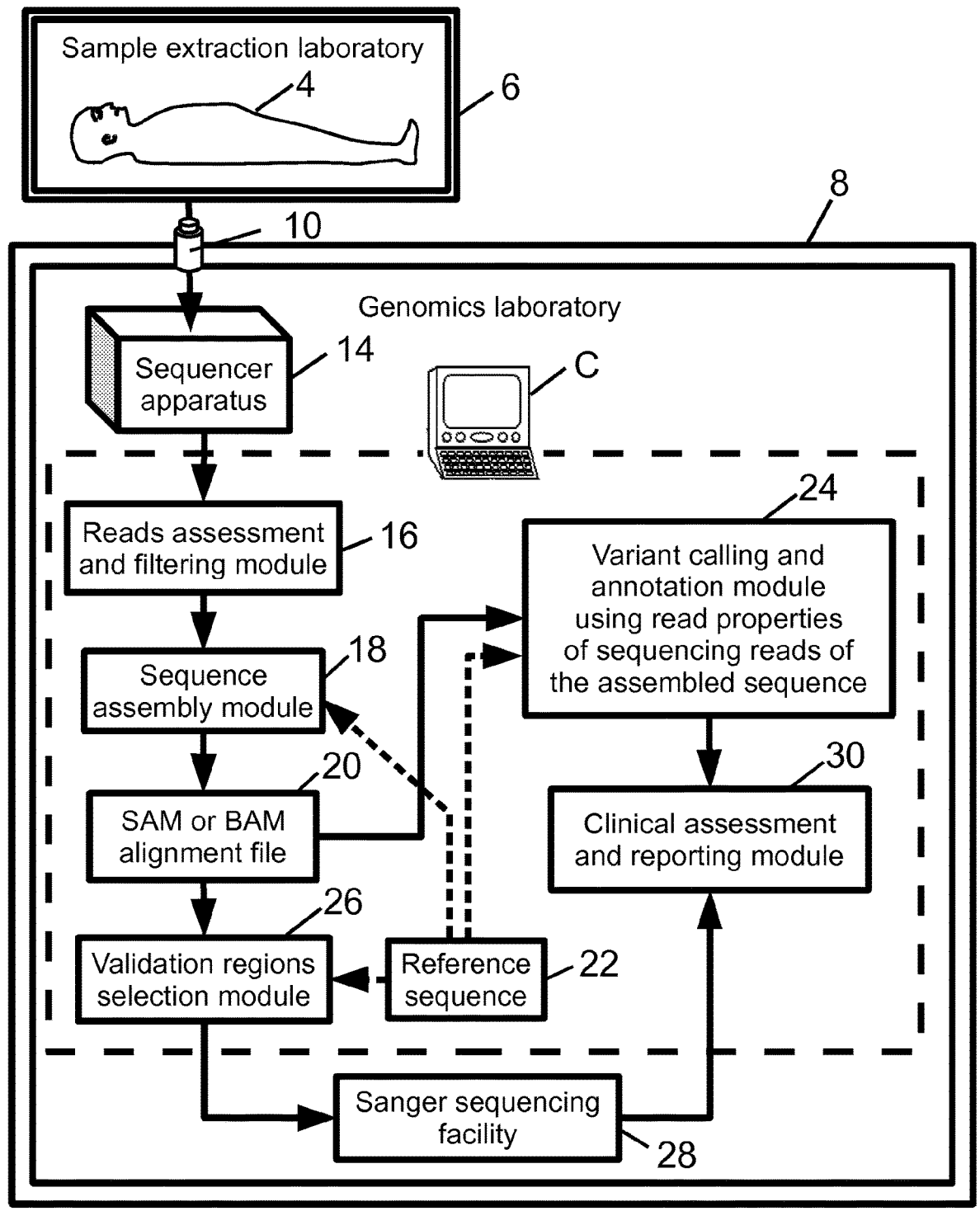

This application is a national stage application under 35 U.S.C. § 371 of International Application No. PCT/IB2012/056911 filed on Dec. 3, 2012 and published in the English language on Jun. 13, 2013 as International Publication No. WO/2013/084133, which claims priority to U.S. Application No. 61/568,336 filed on Dec. 8, 2011 and EP Application No. 11193585.4 filed on Dec. 14, 2011, the entire disclosures of which are incorporated herein by reference.

The following relates to the genetic analysis arts, and to applications of same such as the medical arts, veterinary arts, oncology arts, and so forth.

Genetic analysis finds application in numerous medical and veterinary fields, such as oncology and various genetically related diseases. Conventionally, clinical studies are performed to identify genetic variants whose presence correlates with a particular cancer or disease. Such variants may include, by way of illustrative example: a single-nucleotide polymorphism (SNP); an insertion or deletion (indel); a copy number variation (CNV); a chromosomal aberration or rearrangement; or so forth.

Genetic analysis typically involves the following operations. A tissue sample is acquired from the patient, processed and loaded into a sequencing apparatus which generates sequencing "reads" representing short portions of the genetic sequence typically of order a few dozen to a few hundred bases in length. The sequencing reads are filtered to discard duplicate reads and to remove any reads having unacceptably low coverage and/or unacceptably low base quality, as measured by phred base quality scores for example. A phred score of below 20 is generally used as a criterion for discarding reads. The remaining reads are assembled to generate an aligned genetic sequence. The assembly can be de novo, based on alignment of overlapping portions of sequencing reads, or can be based on mapping of the sequencing reads to a reference sequence while allowing for a certain fraction (e.g., 5-10%) of base mismatches. Variants are detected by comparing the assembled genetic sequence with a reference sequence (possibly the same reference sequence used in mapping-based assembly), and the assembled genetic sequence is annotated to identify variants and their clinical significance (where variant-disease correlation information is available). Validation is performed to detect/characterize sequencing or computational error (if any). A medical report is generated describing the output of the genetic analysis. The medical report is preferably written in terms that a treating physician who may not be well-versed in genetics can readily comprehend, and should include information relating to the validation results.

A key operation in such an analysis is variant identification or "calling". This is the operation in which a detected variant is assessed to identify whether the variant is actually present in the genome of the patient, or is instead an artifact of or error in the sequencing and/or assembly processing. Typically, variant calling is performed based on nucleotide base quality and coverage. The base quality is commonly measured by a phred like quality score. In the case of Sanger sequencing, phred quality scores are calculated from spectrogram data by calculating parameters for the sequenced base such as peak shape and resolution, and comparing these values with an empirically developed look-up table. The phred scores are generally considered to be logarithmically related to the probability that the base was called incorrectly. For example, a phred score (Q) of Q=20 corresponds to a 99% base call accuracy, while Q=30 corresponds to 99.9% accuracy, Q=40 corresponds to 99.99% accuracy, and so forth. Coverage is a metric of the number of reads, and is often expressed in a multiplier form. For example, a coverage of 8× indicates that, on average, a nucleotide was read eight times during the sequencing. In general, higher coverage corresponds to higher read reliability as the coverage indicates redundancy.

So-called "next generation" sequencing (NGS) approaches employ parallel processing techniques that enhance throughput by orders of magnitude. Conventional phred score calculation is generally inapplicable to NGS techniques, but most NGS platforms generate "phred-like" base quality scores that are comparable to or scaled to conventional phred scores computed from spectrogram data. However, they are generally considered to be less reliable than older techniques such as Sanger sequencing. To enhance reliability of NGS, the output is typically validated using a technique such as Sanger sequencing, exome capture, genotyping array, or so forth. Because of the different throughput scales for NGS and these older techniques, the validation is typically performed on a few randomly selected target portions of the (much larger) NGS output.

The high throughput of NGS makes it attractive for clinical applications. However, clinical applications also require high reliability, since medical treatment decisions are based on the clinical NGS results. The lower reliability of NGS compared with earlier techniques thus makes NGS difficult to apply in clinical settings.

The following contemplates improved apparatuses and methods that overcome the aforementioned limitations and others.

According to one aspect, a method comprises: identifying a possible variant in an assembled genetic sequence comprising aligned sequencing reads; computing values of at least one read property for sequencing reads of the assembled genetic sequence; and calling the possible variant conditional upon the computed values of the at least one read property for sequencing reads of the assembled genetic sequence that include the possible variant satisfying an acceptance criterion; wherein the identifying, computing, and calling are performed by an electronic data processing device.

According to another aspect, a method comprises: assembling sequencing reads to generate an assembled genetic sequence; selecting at least one region of the assembled genetic sequence for validation based on a non random selection criterion; and validating the at least one selected region; wherein the assembling and selecting are performed by an electronic data processing device.

According to another aspect, an apparatus comprises a non-transitory storage medium storing an assembled genetic sequence comprising aligned sequencing reads and an electronic processing device configured to perform operations including: identifying a possible variant in the assembled genetic sequence; computing value of at least one read property for reads of the assembled genetic sequence; and calling the possible variant conditional upon the computed values of the at least one read property for sequencing reads of the assembled genetic sequence that include the possible variant satisfying an acceptance criterion.

One advantage resides in more accurate variant calling.

Another advantage resides in greater platform independence in variant calling.

Another advantage resides in validation that is relevant to the genetic analysis.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a genetic analysis system as described herein.

Figure 2:
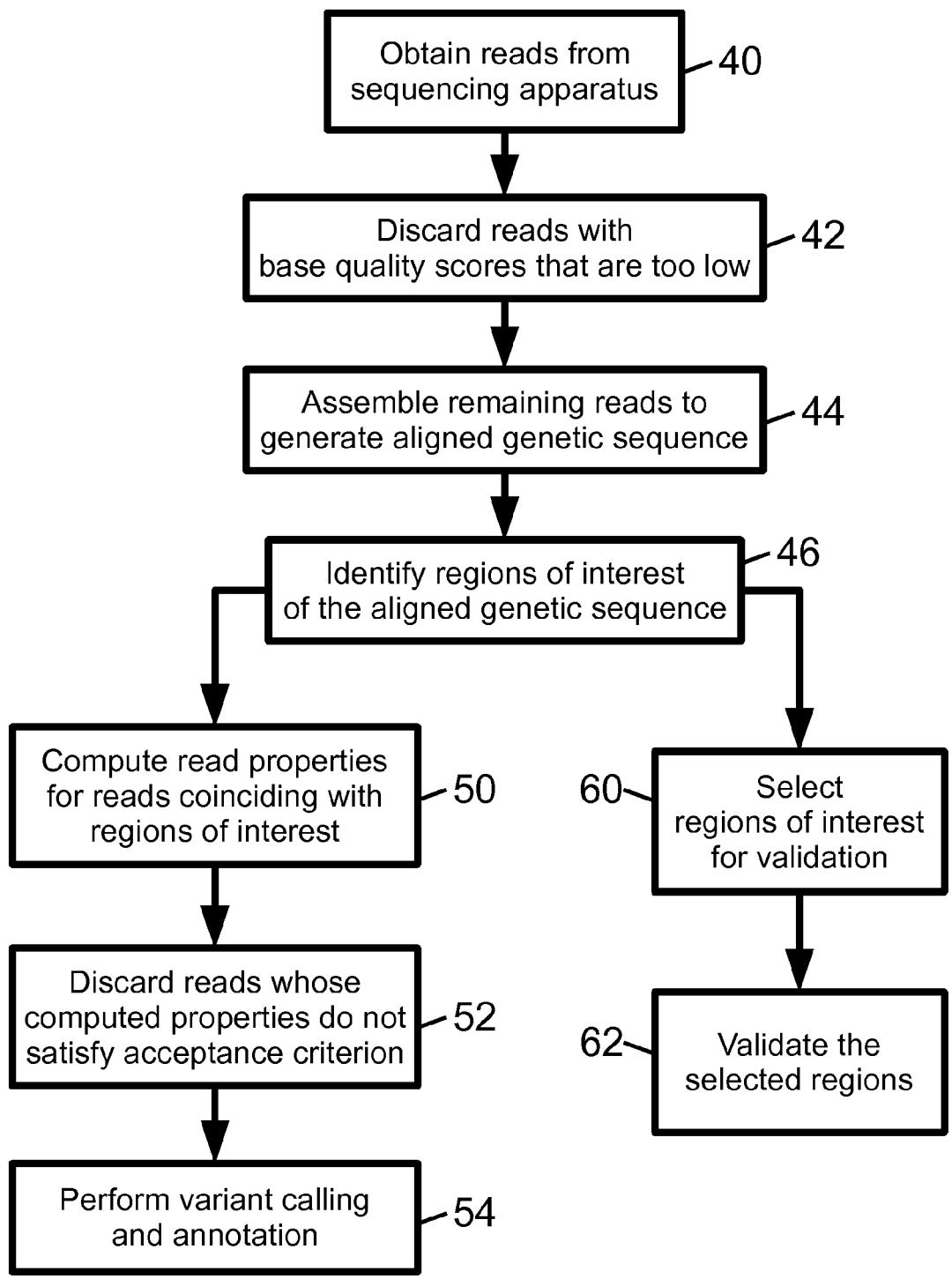

FIG. 2 diagrammatically shows a genetic analysis method suitably performed by the system of FIG. 1.

Figure 3:
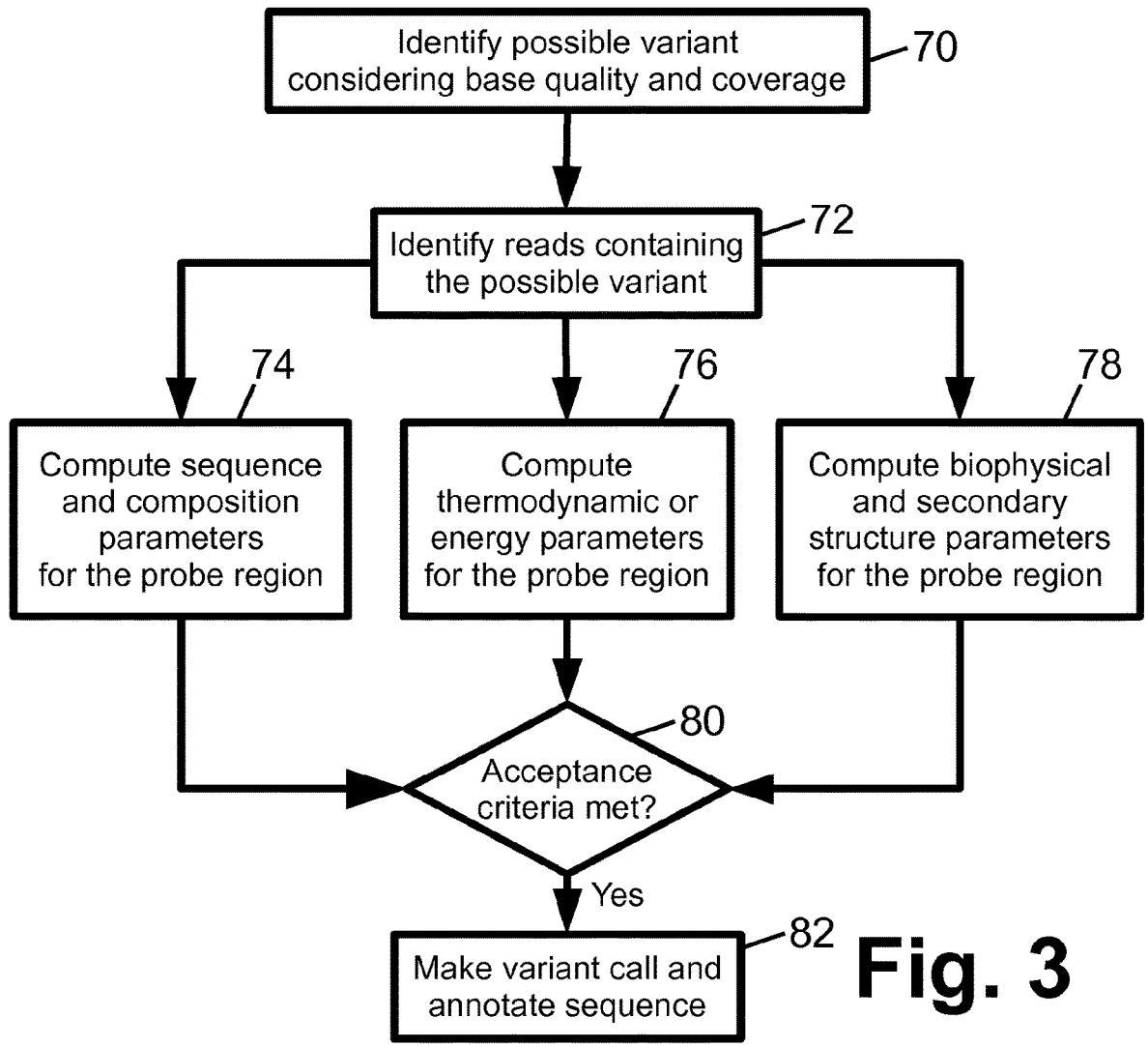

FIG. 3 diagrammatically shows an alternative variant calling method suitably substituted for the variant calling of FIG. 2.

Figure 4:
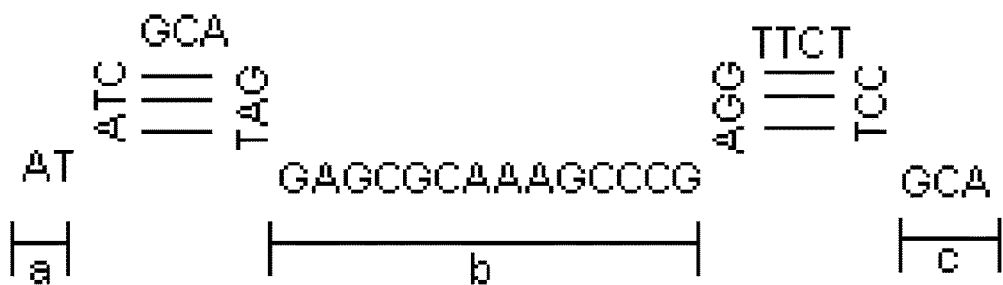

FIG. 4 diagrammatically shows an example of a probe with two loops formed by trimmers.

Figure 5:
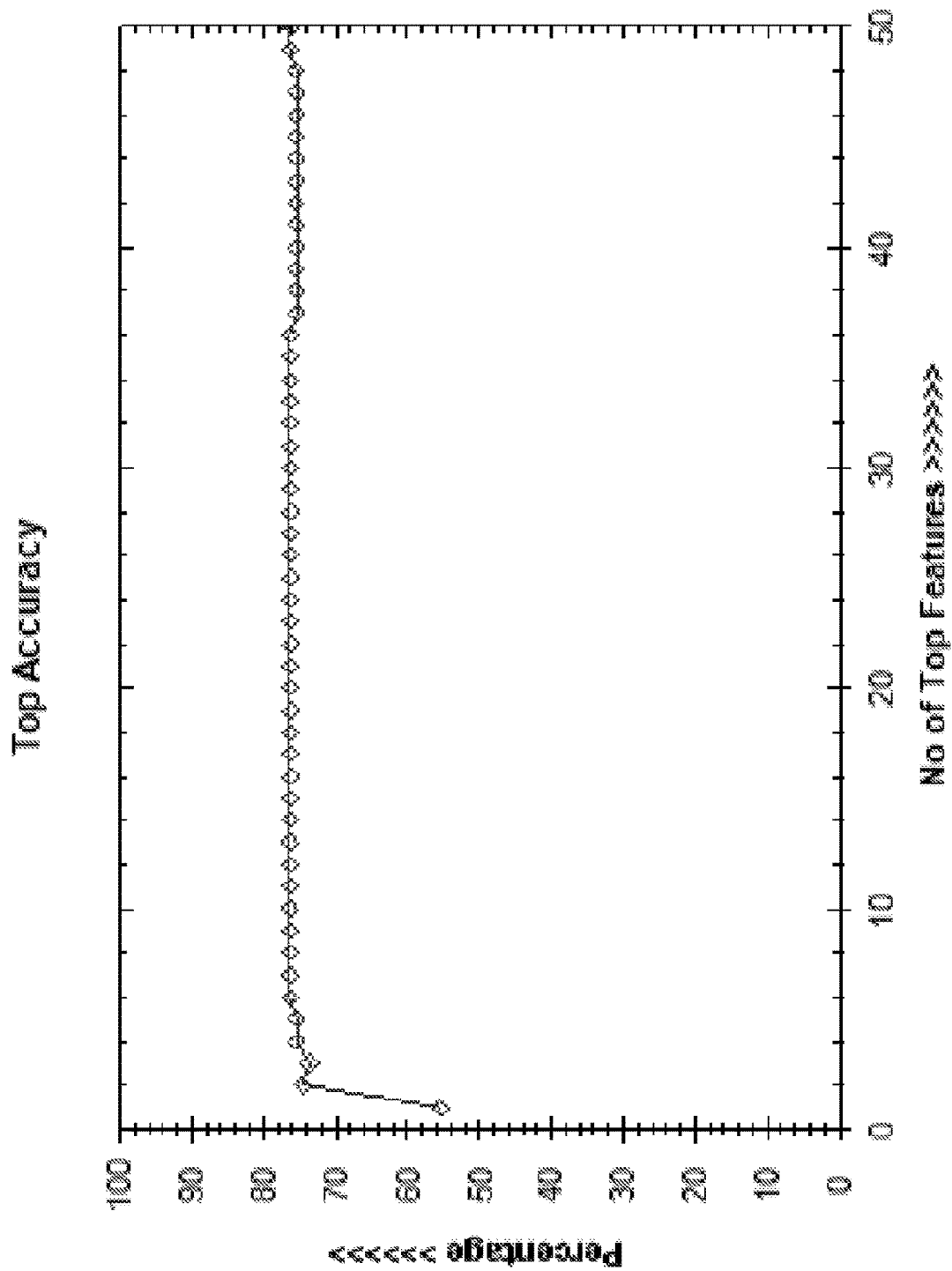

FIG. 5 plots accuracy versus number of top features for the experiment disclosed herein.

Figure 6:
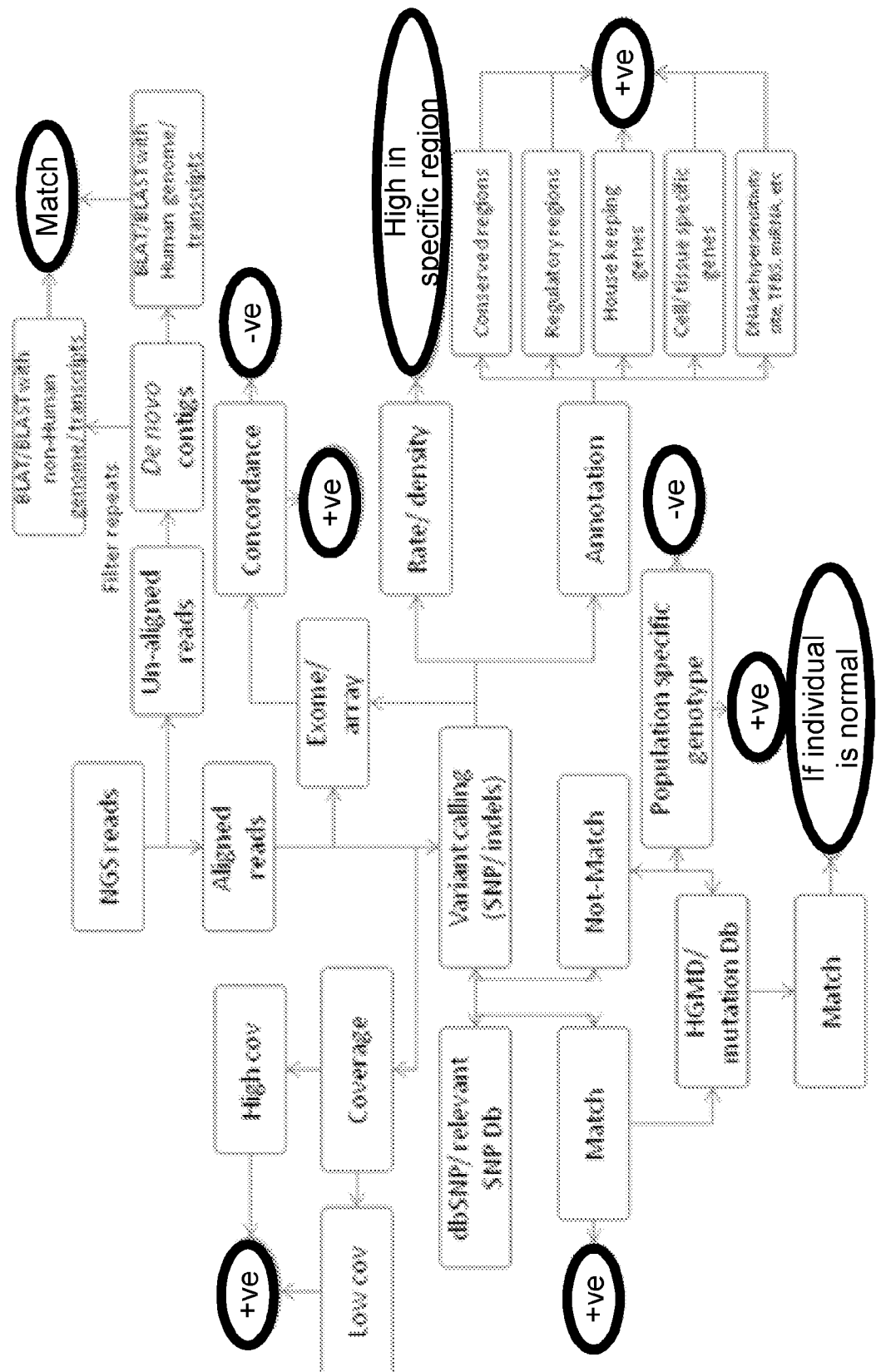

FIG. 6 diagrammatically shows flow of information during next generation sequencing (NGS) processing with points for selecting validation regions for validation of NGS results shown in heavy-lined ellipses.

Variant calling using a combination of base quality score and coverage is generally effective. However, it is recognized herein that there are some disadvantages to this approach. Both base quality score and coverage depend upon the sequencing platform and the alignment algorithm, so that a genetic test reliant upon this approach that is developed for one laboratory may be difficult to transfer to another laboratory. Moreover, sequencing errors tend to propagate into the variant calling, since even a single erroneously called base in a (possible) multi-base variant can result in an erroneous variant call. Thus, the variant call error rate may be substantially higher than the base call error rate predicted by the phred (or other base quality) score. For example, in one study sequencing accuracies of greater than 99.97% for various next generation sequencing (NGS) platforms translated to variant calling accuracies of below 99%, and below 95% for some sequencing platforms. Harismendy et al., "Evaluation of next generation sequencing platforms for population targeted sequencing studies," Genome Biology vol. 10:R32 (2009).

Increasing the coverage should generally reduce variant call errors. However, increasing the coverage is time consuming and incurs greater reagent costs, and may not reduce the variant call error rate to acceptable levels. For example, in one study the error rate in SNP calling using NGS was substantial even for coverage of 20×. Wang et al., "The diploid genome sequence of an Asian individual", Nature vo. 456 pages 60-65 (2008). Without being limited to any particular theory of operation, it is suspected that in some instances this may be a consequence of systematic errors that are not removed by higher coverage, and/or by high coverage variability over the genetic sequence resulting in some sequence portions having substantially lower actual coverage as compared with the reported (statistical) coverage for the complete genetic sequence. See Harismendy et al. Moreover, higher coverage translates into longer sequencing and alignment times, which can reduce the speed advantage of NGS. Validation of randomly selected targets can also fail to detect variant calling problems in regions of an NGS sequence that are not selected as validation targets.

In recognition of these issues, it is known in the art to employ validation of the NGS output by comparison with a more reliable (but slower) technique such as Sanger sequencing ("gold standard"), exome capture, genotyping array, or so forth that produces comparable data. Because of the different throughput scales for NGS and these other techniques, the slower validation technique is typically performed on a few randomly selected target portions of the NGS output. However, such random validation can easily miss significant errors in the NGS sequencing and hence fail to detect erroneous variant calls.

Disclosed herein are improved variant calling techniques that employ assessment of properties of the underlying sequencing reads that contain the possible variant. This approach leverages the fact that the sequencing reads are the actual (i.e., raw) output of the sequencer. The physical DNA or RNA strands that are read are expected to be structurally and thermodynamically stable during the sequencing. The reads are also expected to have properties that fall within a typical range of values for the type of reads under analysis. If read properties computed for the reads of the genetic sequence that include the possible variant indicate that those reads are highly unstable, or deviate from the typical range of values, then it is likely that those reads are erroneous (that is, contain errors). Accordingly, the possible variant contained in those suspect reads may also be erroneous. A further benefit of the disclosed approach is that, by combining a plurality of read properties using a classifier, the variant calling can be tuned during the training of the classifier.

Further disclosed herein are improvements in the validation process. Rather than using a random selection of regions of the NGS output for validation, it is disclosed herein to select the validation regions using a non random criterion that enhances the likelihood that the validating will detect relevant errors, if they exist, in the NGS output. For example, the validation regions may be selected based on a likelihood of error metric, or based on the region being a functional region (and hence of known clinical importance), or based on the region having a low repetitiveness metric (leveraging the common occurrence of repetition in many biological genetic sequences), or based on the region being population specific (these regions are typically more likely to be falsely called as variants), or so forth.

With reference to FIG. 1, a patient 4 undergoes tissue sample extraction in a sample extraction laboratory 6 to generate a sample that is processed by a genomics laboratory 8 to extract, sequence, and analyze DNA and/or RNA of the sample. For example, the sampling laboratory 6 may extract from the subject 4 a tissue sample from a malignant lesion, optionally along with a normal tissue sample extracted from elsewhere in the patient 4. As some other illustrative examples, the sample extraction may comprise a biopsy procedure employing a biopsy needle or other interventional instrument, the plucing of a hair sample to obtain the follicle containing DNA, the drawing of a blood using a hypodermic needle, or so forth. FIG. 1 shows an illustrative extracted tissue sample 10. It is noted that while the illustrative embodiment is operative on patient 4 in a clinical application, in other applications the tissue sample may be extracted from a nonhuman subject such as a veterinary subject, a biology research subject, or so forth. It will also be noted that in illustrative FIG. 1 the sample 10 is represented by an illustrative vial; however, it is to be understood that the sample 10 may in general take any form suitable for the type of tissue that has been sampled, and may be contained or supported by any suitable container or support for that type of tissue. For example, the sample 10 may be a fluid sample, a surface sample (e.g. obtained by oral swabs and disposed on a sterile slide or other suitable surface), or so forth.

At the genomics laboratory 8, the tissue sample 10 is processed by a sequencer apparatus 14 to generate sequencing reads. The sequencer apparatus 14 is preferably a next generation sequencing (NGS) apparatus, and may be a commercial sequencing apparatus such as are available from Illumina, San Diego, Calif., USA; Knome, Cambridge, Mass., USA; Ion Torrent Inc., Guilford, Conn., USA; or other NGS system vendors; however, a noncommercial or custom-built sequencer is also contemplated. The sequencing reads generated by the sequencer 4 are filtered by a filtering module 16 to remove duplicate reads and to discard reads having phred scores below 20 (or below another selected base quality score threshold). The remaining sequencing reads are assembled by a sequence assembly module 18 to generate a genetic sequence that is stored in an alignment file 20 in a Sequence Alignment/Map (SAM) format, a binary equivalent (e.g., BAM) format, or another suitable format stored on a non-transitory storage medium such as a hard disk or other magnetic medium, an optical disk or other magnetic medium, a random access memory (RAM), flash memory, or other electronic storage medium, or so forth. The SAM or BAM format retains the individual sequencing reads and includes further data specifying how the reads form the assembled genetic sequence. The assembly performed by the assembly module 18 can be de novo alignment of overlapping portions sequencing reads, or can be mapping of the sequencing reads to a reference sequence 22 while allowing for a certain fraction (e.g., 5-10%) of base mismatches. In the latter case the reference sequence 22 can be, for example, a standard reference sequence of the human genome in the illustrative case of human patient 4.

In some embodiments the assembled genetic sequence stored in the alignment file 20 is a whole genome sequence (WGS). As used herein, a "whole genome sequence", or WGS (also referred to in the art as a "full", "complete", or "entire" genome sequence), or similar phraseology is to be understood as encompassing a substantial, but not necessarily complete, genome of a subject. In the art the term "whole genome sequence" or WGS is used to refer to a nearly complete genome of the subject, such as at least 95% complete in some usages. In other embodiments, the genetic sequence may represent genetic material that is less than a WGS, for example representing a single chromosome or a portion of a chromosome. Since the sequencer 14 employs high throughput next generation sequencing (NGS), the genetic sequence is typically long, e.g. comprising a contiguous or nearly contiguous sequence of hundreds, thousands, tens of thousands, or more base pairs (bp). The genetic sequence is thus not the type of targeted "sequence" that is typically employed for gene-specific techniques such as single nucleotide polymorphism (SNP) genotyping, for which typically less than 0.1% of the genome is covered. The genetic sequence may represent either DNA (single- or double-stranded) or RNA. A significant distinction between DNA and RNA is that DNA comprises sequences of the bases adenine (A), cytosine (C), guanine (G), and thymine (T); whereas, RNA comprises sequences of the bases adenine (A), cytosine (C), guanine (G), and uracil (U). Said another way, the thymine (T) bases of DNA are replaced by uracil (U) bases in RNA.

A variant calling and annotation module 24 compares the genetic sequence with the reference sequence 22 which may, for example, be a standard reference sequence reported in the literature for the human genome. If the assembly employed mapping, then the assembly and the variant calling typically use the same reference sequence 22, as illustrated in FIG. 1. However, it is also contemplated to use different reference sequences for the assembly and the variant calling, respectively. Comparison of the assembled genetic sequence with the reference sequence 22 enables detection of possible variants (that is, places where the genetic sequence under analysis differs from the reference sequence 22). A possible variant is "called" (that is, accepted as an actual variant for clinical purposes) based on properties of the reads that contain the possible variant, as disclosed herein.

To ensure accuracy, a validation regions selection module 26 selects regions for validation based on a non random selection criterion. The selected validation regions are validated by a suitable validation technique implemented by a suitable system such as an illustrative Sanger sequencing facility 28. (Although the Sanger sequencing facility 28 is shown as part of the genomics laboratory 8 in FIG. 1, it is also contemplated to send the sample out to a different laboratory for validation of the validation regions selected by the selection module 26). Based on the assembled, annotated, and validated genetic sequence, a clinical assessment/reporting module 30 generates a clinical report in a format suitable for review by the physician overseeing treatment of the patient 4. For example, the generated report may identify called variants that are correlated with a particular type of cancer, or may otherwise highlight disease/variant correlations (or the lack of such correlations, as may be the case).

The various processing components including the reads filtering module 16, the sequence assembly module 18, the variant calling/annotation module 24, and the validation regions selection module 26, are suitably embodied by the illustrative computer C or another electronic data processing device such as a desktop computer, notebook computer, network server, or so forth. The clinical assessment/reporting module 30 is also suitably embodied by the computer C or another electronic data processing device, although some aspects of the reporting such as the writing of a summary report directed to the treating physician may be performed manually or semi-manually, for example by a human laboratory technician employed by the genomics laboratory 8. Although illustrative FIG. 1 shows the processing components 16, 18, 24, 26, 30 being embodied by the single illustrative computer C, it is alternatively contemplated to employ different computers to embody these processing components. For example, in some embodiments the filtering module 16 and the sequence assembly module 18 may be embodied by a computer or other electronic data processing device that is integrated with the sequencer 14; while the remaining post-assembly processing, validation, and reporting components 24, 26, 30 may be embodied by a standalone computer or a network server in data communication with the sequencer apparatus.

Further, various embodiments of processing performed by the modules 16, 22, 26, 30 may be physically embodied as a non-transitory storage medium (not shown) storing instructions executable by an electronic data processing device (e.g., the computer C) to perform the disclosed processing. Such a non-transitory storage medium may, for example, comprise a hard disk or other magnetic storage medium, or an optical disk or other optical storage medium, or a flash memory, random access memory (RAM), read-only memory (ROM), or other electronic storage medium, or so forth.

With continuing reference to FIG. 1 and with further reference to FIG. 2, operation of the system of FIG. 1 is described. In an operation 40, sequencing reads are obtained from the sequencing apparatus 14. In an operation 42, the reads assessment/filtering module 16 discards reads with base quality scores that are too low (e.g., having phred scores below 20, in some embodiments). The operation 42 may optionally perform other filtering operations such as removing duplicate reads. In an operation 44, the sequence assembly module 18 assembles the remaining reads to generate an aligned genetic sequence which is stored in the alignment file 20. The assembly may be de novo, based on mapping to a reference sequence, or may be a combination of these (e.g., using mapping where the reference sequence provides coverage and employing de novo alignment elsewhere. Typically some sequencing reads may be "left over", and these unaligned reads are either discarded or stored in the alignment file 20 with suitable annotation indicating their unaligned status.

In an operation 46, regions of interest are identified in the aligned genetic sequence. These regions may be identified in various ways, such as based on known functionality of the region or the possible presence of variants of interest in the region. While selecting regions of interest for further analysis enhances efficiency (especially when the aligned genetic sequence is a WGS), it is also contemplated for the operation 46 to select the entire aligned genetic sequence as the region of interest. On the other hand, a region of interest can be as small as a single base location that has been identified in clinical studies as being a potential location of a single nucleotide variant (SNV) correlative with a disease.

In an operation 50, read properties are computed for reads coinciding with the region (or regions) of interest. A sequencing read "coincides" with a region of interest if it overlaps, contains, or is contained by the region of interest. The read properties may, for example, be thermodynamic properties, structural properties, base compositional properties, or so forth. Various examples are set forth later herein. In an operation 52 any sequencing reads whose computed read properties do not satisfy an acceptance criterion are discarded. In an operation 54, variant calling is performed on the remaining reads (that is, on those reads that pass the read acceptance criteria). Variants can be identified by systematically comparing the aligned genetic sequence base pair-by-base pair (in the case of double-stranded DNA, or base-by-base in the case single stranded DNA or RNA) against the reference sequence 22. This is a comprehensive approach for identifying variants, but can be computationally intensive and may result in many identified variants not having any known disease correlation. Alternatively, in some embodiments the reference sequence 24 includes annotations indicating locations (and optionally compositions) of known disease-correlative variants and the operation 54 examines each such annotated known variant in turn. Some illustrative types of variants include: single nucleotide variants (SNV, also known as single nucleotide polymorphisms, i.e. SNP), insertions or deletions (i.e., indels), copy number variations (CNV's), structural variations (SV), presence or absence of methylation (as compared with the reference sequence 24) or so forth. This can be faster than the base-by-base comparison approach, and additionally the identified variants will usually have a known disease correlation. A combination of these approaches can also be used.

The annotating may include identifying the sub-sequence of bases (or bp's) that deviates from the reference sequence 24 as a variant, and may optionally also label the variant as to type (e.g., SNV, CNV, SV, et cetera). Optionally, the annotating further includes labeling the variant with a disease correlation if such information is available in the reference sequence 24.

With continuing reference to FIG. 2, in an operation 60 the validation regions selection module 26 selects regions of the aligned genetic sequence for validation. The operation 60 does not employ a random selection criterion, but rather a non random selection criterion designed to select validation regions that contain variants, or are functional, or otherwise are of especial interest for validation. In an operation 62, the selected regions are validated, e.g. by the Sanger sequencing facility 28 of FIG. 1.

The operations 46, 50, 52, 54 are suitably performed by the variant calling and annotation module 24 of FIG. 1. In the approach of FIG. 2, regions of interest are selected in the operation 46 and the sequencing reads coinciding with these regions are first tested against the acceptance criterion in operations 50, 52. Only those reads that pass the filtering 50, 52 are then investigated in the operation 54 to identify and call variants. Any variant identified at operation 54 can generally be called immediately since it has already passed the base/coverage criteria (via passing filter 16 of FIG. 1) and the read acceptance filtering (via passing through "second pass" operations 50, 52). This achieves the goal of calling a possible variant conditional upon the computed values of the read properties for sequencing reads of the assembled genetic sequence that include the possible variant satisfying the acceptance criterion. However, in this approach some reads may be tested (and possibly discarded) even though they do not contain any possible variants.

With reference to FIG. 3, in an alternative operation of the variant calling and annotation module 24 of FIG. 1, a possible variant is first identified in an operation 70. At this point only base quality and coverage has been used to filter the possible variants (through operation of the reads assessment/filtering module 16 of FIG. 1). After identifying the possible variant, the sequencing reads that contain the variant are identified in an operation 72. The read properties are only computed for those reads that contain the possible variant. In illustrative FIG. 3, these include: operation 74 computing sequence and composition parameters for reads of the probe region (that is, for those reads containing the possible variant); operation 76 computing thermodynamic or energy parameters for reads of the probe region; and operation 78 computing biophysical or secondary structure parameters for reads of the probe region. Examples of the operations 74, 76, 78 are described later herein. In a decision operation 80, the properties computed in the operations 74, 76, 78 are compared against the acceptance criteria and, if those criteria are met, then the variant calling/annotation module 24 calls the possible variant as an actual variant for medical purposes in operation 82, and makes suitable annotation(s). The approach of FIG. 3 can be computationally more efficient since only reads that contain possible variants are processed by operations 74, 76, 78, 80. However, if there are many possible variants that fail to pass the "second pass" filter operations 74, 76, 78, 80 then the approach of operations 50, 52, 54 of FIG. 2 may be more efficient.

The operation 80 (FIG. 3) differs from the operation 52 (FIG. 2) in that operation 52 filters out potentially erroneous reads, whereas operation 80 decides whether to call a possible variant (in effect, filtering out potentially erroneous possible variants). In one suitable approach for the operation 80, the reads containing the possible variant are filtered in the same way as in operation 52, and the possible variant is then called only if the number of remaining reads (that is, the number of reads that satisfy the acceptance criteria) exceeds a specified minimum coverage for calling the possible variant.

The acceptance criteria employed in operation 52 (FIG. 2) or operation 80 (FIG. 3) are based on values of various read properties. In illustrative FIG. 3 the regional properties whose values are computed include: sequence and composition parameters 74, such as nucleotide frequency, GC clamp, maximum length of continuous bases, or so forth; thermodynamic or energy properties 76 such as enthalpy, entropy, stacking energy, DNA denaturation temperature or energy, duplex stability disrupt energy, or so forth; and biophysical and secondary structure parameters 78 such as dimer formation, cross-dimer formation, hairpin loop formation, bendability, bending stiffness, and so forth. In the operation 80 (or the operation 52 of FIG. 2) the computed values of these read properties are compared against the acceptance criteria. Only if this second-pass acceptance test is also passed (in addition to the "first pass" base quality/coverage filtering provided by the module 16 of FIG. 1) does process flow reach operation 82 (or operation 54 in FIG. 2) at which point a possible variant may be called and annotated.

In the following, some illustrative examples of some suitable read properties are described. These are provided as illustrative examples, and the use of additional, fewer, or other read properties is also contemplated.

Some suitable thermodynamic or sequence composition read properties are as follows. An adverse base pair composition read property value can be computed based on (i) a count of the total number of adenine (A) and thymine (T) bases in the read and (ii) a count of the number of guanine (G) and cytosine (C) bases in the read. (For RNA, thymine is replaced by uracil, i.e. "U"). The ratio of the GC count to the AT (or AU) count should be around 40-60% in typical human DNA or RNA material. An additional compositional read property that may be employed is the number of bases of a single kind that occur in a row anywhere in the read. For example, in some embodiments a property is the number of A or T bases in a row, and if this value is greater than, e.g., six, then the read is not accepted. Such a high number of repeated bases is unusual in a human DNA/RNA sequence, and suggests that it is the result of erroneous sequencing which makes the region (and the possible variant contained therein) untrustworthy so as to preclude calling the possible variant.

The melting temperature ($T_m$) uniformity is one suitable thermodynamic read property. An approximate value for this parameter can be computed as:

$$T_m = 2(A+T) + 4(G+C) \quad (1).$$

A more accurate value for this parameter is given by:

$$T_m = \frac{\Delta H}{\Delta S + R \ln\left(C_1 - \frac{C_2}{2}\right)} - 273.15^\circ \text{ C.}, \quad (2)$$

where $\Delta H$ and $\Delta S$ is the standard enthalpy and entropy, $C_1$ and $C_2$ is the initial concentration of single and complementary strand, and R is the universal gas constant.

Another suitable read property is a GC clamp, which is the number of consecutive guanine (G) and cytosine (C) bases at the 3' end of both the primers. The GC clamp is important for the formation of complex with the target DNA.

Some suitable thermodynamic read properties that play a role in determining the stability of the oligonucleotide probes are: stacking energy; propeller twist; bendability; duplex stability free energy; and DNA denaturation. The dinucleotide base stacking energy represents how easily parts of the DNA de-stack. High value represents an unstable region, and so a read having a high computed stacking energy is filtered out. Regions with low duplex stability free energy content will be more stable than regions with high thermodynamic energy content. Again, if the value is too high this can indicate the read should be filtered out. DNA regions with a low DNA denaturation value are more likely to denature than regions with a higher value. Thus, here a too-low DNA denaturation value may be used to filter a read out.

The dinucleotide propeller twist is the value for the flexibility of the helix. Low values indicate more flexibility. Sections with high bendability values are more bendable than regions with a low value. The trinucleotide bendability model models the bendability of the DNA towards the major groove. The values of these parameters are not readily ascertained as to being "good" or "bad" in terms of the likelihood that the read is a valid read. However, by using these properties as features that are input to a classifier, and training the classifier on labeled data (i.e. reads labeled as "good" or "bad", the classifier can be usefully trained on these read parameters.

Some other factors that affect the stability of the probe are factors pertaining to the internal stability of the oligonucleotides. Typically, stable 5' termini and unstable 3' termini of primers give the best results by reducing false priming on unknown targets. Duplex formation that may initiate DNA synthesis can be prevented by low 3' stability and 5' end must also pair in order to form a stable duplex. Optimal terminal $\Delta G \sim 8.5$ kcal/mol; variation in this reduces priming efficiency. Again, classifier training may be used to optimize the acceptance criteria respective to these parameters.

Some suitable biophysical and secondary structure read properties for use in the acceptance criteria include properties pertaining to hairpin loop formation, duplex stability disrupt energy, DNA bending stiffness; dimer/cross-dimer formation; and self-complementarity. These are addressed in turn.

Regarding hairpin loop formation, a 3' end hairpin with a $\Delta G$ of −2 kcal/mol and an internal hairpin with a $\Delta G$ of −3 kcal/mol is generally tolerated. One suitable read property pertaining to this is the number of nucleotides which do not form a loop formed by trimers (hereinafter "SS feature 1") or quadrimers (hereinafter "SS feature 2"). Another hairpin loop-related read property is the length of the longest sequence with the loops formed by trimers (hereinafter "SS feature 3") or quadrimers (hereinafter "SS feature 4").

With reference to FIG. 4, an example of a probe with two loops formed by trimers is shown. The value of SS feature 1 for FIG. 4 is computed as a+b+c, while the value for SS feature 3 is computed as max(a;b;c). Regions with a value for the high duplex stability disrupt energy will be more stable than regions with a lower energy value. See Breslauer K J, Frank R, Blöcker H, Marky L A, "Predicting DNA duplex stability from the base sequence", Proc Natl Acad Sci USA. 1986 June; 83(11):3746-50. High values for the DNA bending stiffness correspond to DNA regions that are more rigid, while low values correspond to regions that will bend more easily. See Sivolob A V, Khrapunov S N, "Translational positioning of nucleosomes on DNA: the role of sequence-dependent isotropic DNA bending stiffness", J Mol Biol. 1995 Apr. 14; 247(5):918-31.

Dimer/cross-dimer formation can be characterized as a read property as follows. When an oligonucleotide forms intermolecular dimers more readily than hybridizing to target DNA, they reduce the product yield. A 3' end self dimer with a ΔG of −5 kcal/mol and an internal self dimer with a ΔG of −6 kcal/mol is generally tolerated. A suitable measure of probe self complementarity is a palindrome score of less than 7 bp.

In the following, some actually performed experiments are described.

Whole genome sequencing was performed as follows. Paired end libraries were constructed for WGS using the NEBNext DNA sample Prep Master Mix Set 1 with Illumina Standard Paired-end oligos. Illumina 115 base pair paired end read data were produced over multiple runs. A total of 1,267,651,634 pair end reads were produced from WGS. Data were processed using the Illumina pipeline v1.5/v1.6 for base calling. Reads which passed Illumina filtering were aligned to the human reference genome assembly (UCSC Hg19) with the Burrows Wheelers Aligner (BWA), configured to allow two mismatches in a 30 bp seed (Li et al., 2009). Duplicate read pairs were removed to counteract PCR artifacts generated during sample preparation. The mean coverage of the mapped bases after whole genome assembly was ~28×.

Post-alignment SNV calling was performed with SAMtools, using a minimum SNV quality score of 20 and a minimum read depth of 20× (Li et al., 2009). SNVs in close proximity to insertion/deletion variants (indels), SNVs in regions of excessive read depth and regions with multiple SNV calls within a 10 base pair window were removed. A total of 3,291,501 and SNVs were called for the whole genome. A list of SNVs was then selected and multiple thermodynamic parameters were extracted. SNVs were also selected randomly for validation using Sanger di-deoxy capillary sequencing method.

Reads were then classified into two categories: (1) Category 1, in which the genotype call from WGS and Sanger sequencing matched; and (2) Category 2, in which the genotype call from WGS and Sanger sequencing did not match. There reads were then subjected to feature extraction, selection and classification. The feature extraction extracted the base compositional, thermodynamic, and secondary structure features described previously herein. The feature selection employed support vector machine ranked features extraction (SVM-RFE) and nearest neighbor ranked features (NN-RF). A total of 3219 features were extracted and analyzed in various regions of probes including the 3' end, 5' end and in the middle of the probe. After that a classification method was applied on them in order to discriminate a good probe from bad.

Support Vector Machines (SVMs) have been used for various classification purposes. They map data into a higher dimensional space that provides better separation between the classes and find a hyperplane that provides the maximum margin. Given training vectors $x^k \in R^n$, k=1, ..., m in two classes, and a vector of label $y \in R^m$ such that $y^k \in \{1,-1\}$, SVM solves an optimization problem:

$$\min_{w,b,\xi} \frac{1}{2} w^T w + C \sum_{k=1}^{m} \xi_k, \quad (3)$$

subject to:

$$y_k(w^T \phi(x_k) + b) \geq 1 - \xi_k \quad (4)$$

and $$\xi_k \geq 0, k = 1, \ldots, m, \quad (5)$$

where the training data are represented in a higher dimensional space by a kernel function φ, and C is a penalty parameter on the training error. For any testing vector x, the decision function is:

$$f(x) = sgn(w^T \phi(x) + b) \quad (6).$$

Feature selection was performed using as an accuracy measure. The features calculated from the probes have to be optimally selected to result in a better classifier. It is possible that some of the features may degrade the performance of the classifier. The strategy employed in the experiments was to identify the top features and the use them to train and test the classifier. F-score offers a convenient representation where features can be ranked based on their discriminative power between the good and bad probes. Given training vectors $x^k \in R^n$, k=1, ..., m, if the number of good and bad probes are n+ and n-respectively, then the F-score of the ith features is calculated as:

$$F(i) = \frac{(\bar{x}_i^{(+)} - \bar{x}_i)^2 + (\bar{x}_i^{(-)} - \bar{x}_i)^2}{\frac{1}{n_+ - 1} \sum_{k=1}^{n_+} (x_{k,i}^{(+)} - \bar{x}_i^{(+)})^2 + \frac{1}{n_- - 1} \sum_{k=1}^{n_-} (x_{k,i}^{(-)} - \bar{x}_i^{(-)})^2}, \quad (7)$$

where the symbols $\bar{x}_i$, $\bar{x}_i^{(+)}$, $\bar{x}_i^{(-)}$ are the mean of the ith feature for the whole, good, and bad probe data sets respectively. $x_{k,i}^{(+)}$ is the ith feature of the kth good probe and $x_{k,i}^{(-)}$ is the ith feature of the kth bad probe. The numerator indicates the discrimination between the good and bad probe sets and the denominator indicates the one within each of the two sets. Higher F-score value suggests that the feature is more discriminative.

A total of 3219 features were computed from the reads of both the Category 1 and 2. The features were scaled to the range 0 to 1 before computing the F-score values for them. Experiments revealed that the top features varied across the datasets. In most of the cases, those features expected to be the priority ones (based on prior experience) came out in the top feature list. Table 1 shows the top ten features identified for various datasets. It should be noted here that the length of the probes varied across these datasets and some of the features may not be relevant for the shorter ones. However, it may be noticed that there is some overlap between the top features identified for various data sets.

TABLE 1

Top features identified for reads that were validation positive and validation negative

| Thermodynamic | | Secondary structure | |
|---|---|---|---|
| Feature | F score | Feature | F score |
| Propeller (complete) | 0.463217 | Free at 5'end in pentamer loop (second) | 0.022776 |
| Tm: Salt 50 NucAcid 50 (complete) | 0.372434 | Free at 3'end in tetra loop | 0.014256 |
| Propeller (5'end) | 0.327285 | Free at 5'end in tetra loop (first) | 0.014256 |
| Content (complete) | 0.298143 | Free at 5'end in trimer loop | 0.014045 |
| Trinucleotide (complete) | 0.293189 | Free at 5'end in trimer loop (second) | 0.011524 |
| Stiffness (complete) | 0.27979 | maximum in trimer loop | 0.008427 |
| Denaturation (complete) | 0.26369 | minimum in tetra loop | 0.004824 |
| Free energy (complete) | 0.24907 | minimum in trimer loop | 0.003269 |
| Stacking energy (complete) | 0.247236 | maximum in pentamer loop | 0.002597 |
| Content (5'end) | 0.225024 | Free at 3'end in pentamer loop | 0.002251 |

SVM classification using F-score was done in the experiments as follows. The F-score values for the features were sorted in descending order and a SVM classifier was trained using them by incrementing the number of top features in steps of n (typically taken as 10). The number of top features may be selected based on the accuracy obtained by evaluating the classifier on test data. The optimal set of features is the one that results in the highest classification accuracy.

FIG. 5 plots the accuracy versus number of top features obtained for one such dataset. SNVs form different categories shows a good separation and is a good indicator to be used for determining the accuracy of the SNV generated from a set of reads from the WGS dataset.

In the foregoing experiments, SNVs were selected randomly for validation using Sanger di-deoxy capillary sequencing method. As discussed with reference to the validation regions selection module 26 of FIG. 1, it is disclosed herein to select regions for validation using a non random selection criterion.

With reference to FIG. 6, steps and check points for extraction of target regions for validation is diagrammatically shown. FIG. 6 shows flow of information with points for selecting validation regions for validation of NGS results shown in heavy-lined ellipses. Based on bandwidth/resources for validation (e.g., the throughput of the Sanger sequencing facility 28 of FIG. 1), a number of target regions may be selected at each step or check point. The selection criteria for selecting validation regions may include: selection based on a likelihood of error metric for the region in order to validate any area having a high likelihood of error; selection based on the region being a functional region (that is, a functional region in the genome); selection based on a low base repetition metric for the region in order to validate regions that are substantially devoid of repetitive regions; selection based on the region being a population-specific region (that is, having population specific information, which can be erroneously detected as a genetic variant); selection based on the region containing at least one annotation indicating a variant; regions having different structural characteristics; or so forth.

TABLE 2

SNP's selected for validation

| Chr | hg19 start | hg19 end | rsid | hg18 start | s* | sample | Ref | Cov | B |
|---|---|---|---|---|---|---|---|---|---|
| chr15 | 28705279 | 28705280 | rs7163702 | 26500067 | + | V16 | C | 52 | C |
| chr17 | 16287670 | 16287671 | rs41447048 | 16228395 | + | V16 | A | 37 | A |
| chr19 | 22841788 | 22841789 | rs2957833 | 22633628 | + | V16 | t | 32 | T |
| chr19 | 54781843 | 54781844 | rs4022330 | 59473655 | + | V16 | C | 5 | C |
| chr6 | 2547684 | 2547685 | rs10456057 | 2492683 | + | V16 | A | 68 | A |
| chr6 | 2641546 | 2641547 | rs2596437 | 2586545 | + | V16 | A | 39 | A |

(s* = strand; B = WGS base call)

Tables 2, 3, and 4 provide examples of target single nucleotide polymorphism (SNP), indel, and structural variation (SV) regions that were selected for validation based on the foregoing non random criteria.

The invention has been described with reference to the preferred embodiments. Obviously, modifications and alterations will occur to others upon reading and understanding the preceding detailed description. It is intended that the

TABLE 3

Indels selected for validation

| Chr | Ref Position | Gene | Refseq Acessions | Strand | Reference Position | Continuation Row Index |
|---|---|---|---|---|---|---|
| 17 | 45234406 | CDC27 | NM_001114091 | − | 45234406 | 1 |
| 19 | 45016990 | CEACAM20 | NM_001102599 | − | 45016990 | 2 |
| 1 | 152195728 | HRNR | NM_001009931 | − | 152195728 | 3 |
| 19 | 41123093 | LTBP4 | NM_001042544 | + | 41123093 | 4 |
| 17 | 34100350 | MMP28 | NM_024302 | − | 34100350 | 5 |
| 11 | 17333663 | NUCB2 | NM_005013 | + | 17333663 | 6 |
| 12 | 1.13E+08 | OAS1 | NM_016816 | + | 1.13E+08 | 7 |
| 6 | 31106500 | PSOR1 | NM_014068 | + | 31106500 | 8 |
| 17 | 7470285 | SENP3 | NM_015670 | + | 7470285 | 9 |
| 11 | 1.19E+08 | SLC34 | NM_001467 | − | 1.19E+08 | 10 |

| Continuation Row Index | Allele in Sample | Reads1/Reads2 | Homo/Het | dB SNP ID | Exome data | Effect |
|---|---|---|---|---|---|---|
| 1 | */−T | 670/123 | Het | — | Agrees | Frameshift |
| 2 | −A/−A | 21/1 | Homo | — | Agrees | Frameshift |
| 3 | −A/−A | 25/6 | Homo | — | NC | Frameshift |
| 4 | +G/+G | 24/4 | Homo | — | Agrees | Frameshift |
| 5 | +G/+G | 31/1 | Het | — | Agrees | Frameshift |
| 6 | A | 33//0 | Homo | rs2521998 | NA | Splice Signal |
| 7 | A | 83//0 | Homo | rs10774671 | NA | Splice Signal |
| 8 | +C/+C | 25/3 | Het | — | Agrees | Frameshift |
| 9 | −A/−A | 22/3 | Het | — | Agrees | Frameshift |
| 10 | −G/−G | 54/5 | Homo | — | Agrees | Frameshift |

TABLE 4

SV selected for validation

| Chr | Start | End | SV type | length | Homo/Het | deviant reads | Continuation Row Index |
|---|---|---|---|---|---|---|---|
| 1 | 152555546 | 1.53E+08 | Del | 32189 | Homo | 25 | 1 |
| 1 | 152555546 | 1.53E+08 | Del | 32189 | Homo | 25 | 2 |
| 20 | 62596234 | 62597524 | Del | 116 | Homo | 15 | 3 |
| 22 | 24274145 | 24311299 | Del | 37154 | Homo | 25 | 4 |
| 22 | 24274145 | 24311299 | Del | 37154 | Homo | 25 | 5 |

| Continuation Row Index | total reads | Gene | Coding | Strand | Description |
|---|---|---|---|---|---|
| 1 | 25 | LCE3B | protein-coding | + | late cornified envelope 3B |
| 2 | 25 | LCE3C | protein-coding | + | late cornified envelope 3C |
| 3 | 16 | ZNF5B | protein-coding | − | zinc finger protein 512B |
| 4 | 25 | GST2B | protein-coding | − | glutathione S-transferase theta 2B (gene/pseudogene) |
| 5 | 25 | DDTL | protein-coding | + | D-dopachrome tautomerase-like |

The invention claimed is:

1. A method comprising:
   identifying a possible variant in an assembled genetic sequence comprising aligned sequencing reads;
   computing values of at least one read property for sequencing reads of the assembled genetic sequence; and
   calling the possible variant conditional upon the computed values of the at least one read property for sequencing reads of the assembled genetic sequence that include the possible variant satisfying an acceptance criterion;
   wherein the possible variant is classified as accepted or rejected using a classifier operating on the computed values of the plurality of read properties for the reads that include the possible variant; and wherein the possible variant is called only if the possible variant is classified as accepted, wherein classifying is performed using support vector machine classification using F-score;
   wherein the identifying, computing, and calling are performed by an electronic data processing device.

2. The method of claim 1 wherein the at least one read property includes at least one base composition property.

3. The method of claim 1 wherein the at least one read property includes at least one thermodynamic property.

4. The method of claim 1 wherein the at least one read property includes at least one energy property wherein the energy property is indicative of read stability.

5. The method of claim 1 wherein the at least one read property includes at least one secondary structure property.

6. The method of claim 1 further comprising:
   assembling a set of sequencing reads to generate the assembled genetic sequence;
   wherein sequencing reads that do not satisfy base quality score and coverage criteria are discarded and are not included in the assembled genetic sequence; and
   wherein the assembled genetic sequence comprises a whole genome sequence.

7. An apparatus comprising:
   a non-transitory storage medium storing an assembled genetic sequence comprising aligned sequencing reads; and
   an electronic processing device configured to perform operations including:
   identifying a possible variant in the assembled genetic sequence;
   computing value of a plurality of read properties for reads of the assembled genetic sequence; and
   calling the possible variant conditional upon the computed values of the at least one read property for sequencing reads of the assembled genetic sequence that include the possible variant satisfying an acceptance criterion;
   wherein the possible variant is classified as accepted or rejected using a classifier operating on the computed values of the plurality of read properties for the reads that include the possible variant; and wherein the possible variant is called only if the possible variant is classified as accepted; wherein classifying is performed using support vector machine classification using F-score.

8. The apparatus of claim 7 wherein the at least one read property includes at least one read property selected from a group consisting of: a base composition property, a thermodynamic property, an energy property, and a secondary structure property.

9. A method comprising:
   identifying a possible variant in an assembled genetic sequence comprising aligned sequencing reads;
   computing values of at least one read property for sequencing reads of the assembled genetic sequence wherein the at least one read property includes at least one base composition property of the sequencing reads; and
   calling the possible variant conditional upon the computed values of the at least one read property for sequencing reads of the assembled genetic sequence that include the possible variant satisfying an acceptance criterion;
   wherein the possible variant is classified as accepted or rejected using a classifier operating on the computed values of the plurality of read properties for the reads that include the possible variant and the possible variant is called only if the possible variant is classified as accepted; and
   wherein the identifying, computing, and calling are performed by an electronic data processing device.

10. The method of claim 9 wherein the at least one read property further includes at least one thermodynamic property of the sequencing reads.

11. The method of claim 9 wherein the at least one read property further includes at least one energy property of the sequencing reads wherein the energy property is indicative of read stability.

12. The method of claim 9 wherein the at least one read property further includes at least one secondary structure property of the sequencing reads.

13. The method of claim 9 wherein the sequencing reads are DNA reads and the base composition property comprises a function of (i) the count of adenine and thymine bases in the sequencing reads and (ii) the count of guanine and cytosine bases in the sequencing reads.

14. The method of claim 9 wherein the sequencing reads are RNA reads and the base composition property comprises a function of (i) the count of adenine and uracil bases in the read and (ii) the count of guanine and cytosine bases in the read.

15. The method of claim 9 further comprising:
   generating a clinical report identifying called variants, wherein the generating is performed by the electronic data processing device.

16. The method of claim 9 further comprising:
   generating a clinical report identifying called variants that are correlated with a particular type of cancer, wherein the generating is performed by an electronic data processing device.

* * * * *